United States Patent [19]
Klemp et al.

[11] Patent Number: 5,547,497
[45] Date of Patent: Aug. 20, 1996

[54] APPARATUS FOR GAS CHROMATOGRAPHY

[75] Inventors: Mark A. Klemp, Swartz Creek; Anita J. Peters, Farmington Hills, both of Mich.

[73] Assignee: Chromatofast, Inc., Ann Arbor, Mich.

[21] Appl. No.: 174,129

[22] Filed: Dec. 28, 1993

Related U.S. Application Data

[63] Continuation-in-part of Ser. No. 953,893, Sep. 30, 1992, Pat. No. 5,288,310.

[51] Int. Cl.$^6$ .................................................. B01D 15/08
[52] U.S. Cl. ........................... 96/104; 73/23.41; 95/82; 95/85; 95/86; 95/87; 96/105; 96/106
[58] Field of Search ............................... 95/82, 86, 87, 95/85, 89; 96/101, 102, 104, 105, 106, 107; 73/23.41, 23.22, 23.35

[56] References Cited

U.S. PATENT DOCUMENTS

| | | | |
|---|---|---|---|
| 3,225,520 | 12/1965 | Burow | 95/87 |
| 3,225,521 | 12/1965 | Burow | 95/87 |
| 3,298,786 | 1/1967 | Hinswark | 73/23.41 |
| 3,301,040 | 1/1967 | Levy et al. | 73/23.41 |
| 3,356,458 | 12/1967 | Steinle et al. | 73/23.41 |
| 3,698,869 | 10/1972 | Condon | 96/106 |
| 4,180,389 | 12/1979 | Paul | 95/11 |
| 4,954,150 | 9/1990 | Etzweiler | 96/106 |
| 5,032,151 | 7/1991 | Klein et al. | 95/89 |
| 5,096,471 | 3/1992 | Sacks et al. | 96/105 |
| 5,141,532 | 8/1992 | Sacks et al. | 95/87 |
| 5,141,534 | 8/1992 | Sacks et al. | 96/102 |
| 5,288,310 | 2/1994 | Peters et al. | 96/105 |

FOREIGN PATENT DOCUMENTS

4132358C1 11/1992 Germany.

OTHER PUBLICATIONS

*Use of a Backflushable Pre–Column to Maintain the Performance of an Aluminum Oxide Porous–Layer Open Tubular Fused Silica Column for the Determination of 1,3–Butadience in Air,* Lunsford and Gegnon, Journal of High Resolution Chromatography & Chromatography Communications, vol. 10, Feb. 1987.

*Cryofocusing Inlet with Reverse Flow Sample Collection for Gas Chromatography,* Mark A. Klemp, Michael L. Akard, and Richard D. Sacks, 266b Analytical Chemistry, 65 (1993) Sep. 15, No. 18, Washington, D.C. U.S.

*Primary Examiner*—Jay H. Woo
*Assistant Examiner*—Duane S. Smith
*Attorney, Agent, or Firm*—Harness, Dickey & Pierce, P.L.C.

[57] ABSTRACT

A gas chromatograph system including a cold trap having two portions, a capillary tube and a porous layer open tubular (PLOT) column, for substantially simultaneously trapping lower and higher boiling point gasses. The capillary tube enables cold trapping of lower boiling point gasses while the PLOT column enables cold trapping of higher boiling point gasses. The capillary tube interconnects at one end to an analytical column and a sample gas source and interconnects at its other end to a first end of the PLOT column. The other end of the PLOT column interconnects to a carrier gas source and a vacuum source. The capillary tube and PLOT column are both positioned within a temperature controlled environment of the cold trap. During the collection mode, the temperature control device maintains a relatively low temperature to condense the sample components. During injection of the sample from the cold trap to the analytical column, the temperature control device maintains a relatively high temperature to vaporize the sample components.

36 Claims, 6 Drawing Sheets

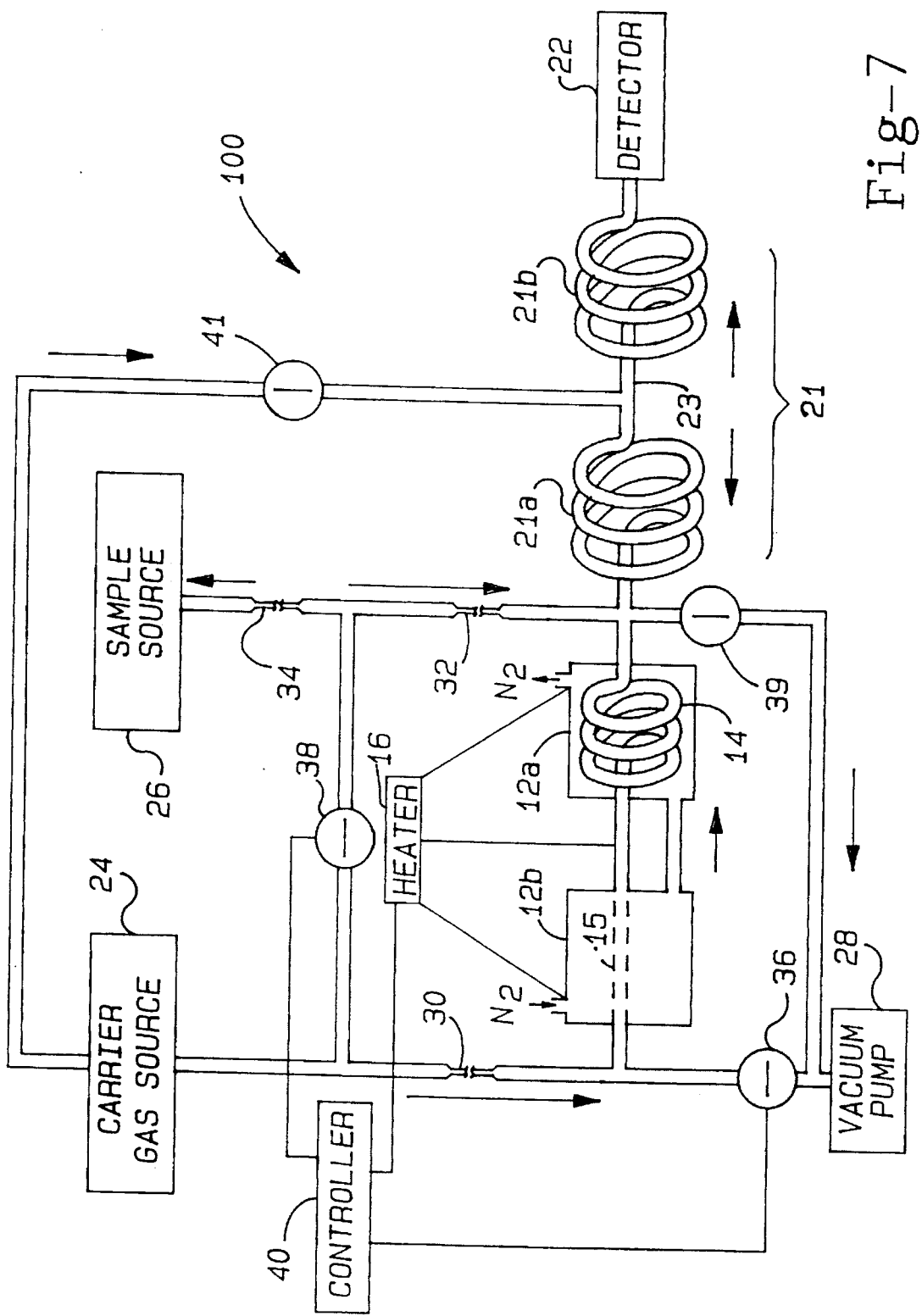

APPARATUS FOR GAS CHROMATOGRAPHY

CROSS REFERENCE TO RELATED APPLICATION

This application is a continuation-in-part of U.S. application Ser. No. 953,893 filed on Sep. 30, 1992 entitled "Adsorbent Trap for Gas Chromatography" now issued as U.S. Pat. No. 5,288,310.

BACKGROUND AND SUMMARY OF THE INVENTION

This invention relates to a gas chromatography system and methods for increasing the speed, operational flexibility, and accuracy of gas chromatography procedures.

Gas chromatography is a widely employed technique for the separation and analysis of complex mixtures of volatile organic and inorganic compounds. The mixture is separated into its components by eluting them from a column having a sorbent by means of a moving gas.

Gas chromatography procedures can be classified into two major divisions: gas-liquid chromatography and gas-solid chromatography. Gas-liquid chromatography is presently the most widely employed type and incorporates a nonvolatile liquid sorbent coated as a thin layer on an inert support structure, generally a capillary tube. The moving gas phase called the carrier gas flows through the chromatographic analytical column. The analyte partitions or divides itself between the moving gas phase and the sorbent and moves through the column at a rate dependent upon the partition coefficient or solubility of the analyte components. Various types of analytical columns are employed such as tubular glass or stainless steel capillary tubes. In use, the analyte is introduced at the entrance end of the column within the moving carrier gas stream. The components making up the sample become separated along the column and elute from the exit end of the column at intervals and in concentrations characteristic of the properties of the analyte components. A detector, for example, a thermal conductivity detector or a flame ionization detector (FID) at the exit end of the column responds to the presence of analyte components. Upon combustion of the eluted material in the FID, charged species are formed in the flame. The flame behavior is monitored through a biased ion detector which, along with associated electronics, produces a time versus magnitude trace of the detector output. The trace for a complex mixture includes numerous peaks of varying intensity. Because individual constituents of the analyte produce peaks at characteristic times having magnitudes that are a function of the constituent concentration, much information is gained through an evaluation of the chromatogram.

Various approaches are presently used for introducing a sample into the separation column. In one general type of gas chromatography system, a thermal focusing chamber or cold trap is employed. The cold trap is typically a vessel containing a cold gas such as nitrogen and having a capillary sample tube passing through it which conducts the analyte. By exposing incoming analyte to the low temperatures within a cold trap, the analyte components condense on the capillary tube. When it is desired to inject a sample into the column for separation, the temperature of the sample tube passing through the cold trap is increased rapidly thus vaporizing the sample. The carrier gas stream which continually flows through the trap then injects the analyte into the column for separation.

In a typical gas chromatography system of the type employing a thermal focusing chamber, during the trapping mode of operation, a single cold trap having a capillary tube at the inlet end of the cold trap sample tube (i.e., in the direction of carrier gas flow during injection) traps the incoming analyte. After heating the cold trap sample tube, the sample components must traverse the entire length of the sample tube before introduction into the column. The sample flow circuit regions between where the component is vaporized and the beginning of the column constitute system "dead volume" which is undesirable because it results in broadening of the injected analyte in terms of the time duration over which it is presented to the inlet end of the column. Dead volume adversely affects system resolution and efficiency.

Today there is increased emphasis toward so called "high-speed gas chromatography" or "high speed GC". Applications include process stream monitoring, environmental monitoring, and engine exhaust gas analysis. Ideally such systems would be able to perform an analysis within several seconds which previously took several minutes or more. Increasing the speed of analysis can be achieved by providing a relatively short separation column or by using other techniques for causing components of interest to traverse the column quickly. In order to provide useful information, the individual analyte components must elute separately at the detector, thus producing distinct peaks. As the length of time that the sample is injected at the inlet end of the column increases, the peaks produced by elution of the components tend to broaden. It is, therefore, essential that a narrow sample "plug" be presented at the column during injection in order to provide gas chromatography evaluation in a small period of time. It is for this reason that the dead volume associated with conventional cold trap type gas chromatography systems is a disadvantage. In gas chromatography systems of the type described previously which employ a thermal focusing chamber or cold trap, it must be understood that the entire length of the cold trap sample tube cannot be maintained ideally at a uniform constant temperature, either during the collection or injection modes. In fact, a temperature gradient exists at the inlet and outlet ends of the cold trap capillary tube. Because during the collection mode of operation, the analyte condenses near the inlet end of the capillary tube (in terms of the direction of flow of carrier gas during injection), it is necessary to insure that region is sufficiently heated to vaporize all of the components of interest of the mixture during the injection step. This requirement leads to some portions of the cold trap sample tube being heated to a significantly higher temperature than is necessary to vaporize the sample collected at the inlet end of the sample tube. Furthermore, the analyte is exposed to the excessive temperatures for the length of time necessary to conduct them entirely through the focussing chamber. These excessive temperatures and the significant "residence time" in the sample tube have been related to decomposition of analyte components. Accordingly, instead of components in their natural state being ejected from the column, these components become fragmented into parts of the initial molecule. Such decomposition of the sample significantly complicates analysis and can render the generated chromatogram of little value in certain types of evaluation. An improved cold trap addressing many of the above described disadvantages disclosed in U.S. Pat. No. 5,141,534 which is a continuation-in-part of U.S. patent application Ser. No. 590,174, now U.S. Pat. No. 5,096,471, both herein incorporated by reference.

In a reverse flow cold trapping apparatus, during the trapping mode of operation, the more volatile (lower boiling point) compounds have a tendency to completely traverse the cold trap before the less volatile (higher boiling point) compounds have entered the cold trap. The high rate of traversal of the low boiling point compounds makes it difficult to cryofocus (or cold trap) the lower boiling point and the higher boiling point compounds substantially simultaneously. This generally results in a loss of lower boiling point compounds when attempting to cryofocus and perform detection on the higher boiling point compounds as well. Consequently, it would be extremely beneficial if it were possible to develop a cold trap apparatus which decreases the rate of traversal through the cold trap of the lower boiling point compounds so that the higher boiling point compounds may also be cryofocused substantially simultaneously.

The first described embodiments of a gas chromatography system in accordance with the present invention improves over present devices with respect to each of the previously described areas. In a first embodiment, a cold trap is provided which has a capillary tube for trapping higher boiling point compounds in a first portion of the trap and a porous layer open tubular (PLOT) column to trap the lower boiling point compounds. One end of the capillary tube is positioned in proximity to an analytical column, and sample gas originating from a sample gas source is introduced into the cold trap at this end during collection mode. The other end of the capillary tube interconnects with a first end of the PLOT column, the second end of which interconnects to a vacuum source. The cold trap includes a temperature control source which maintains the cold trap at a low temperature during the collection mode and increases the temperature of the cold trap to vaporize the trapped sample during injection mode. The flow of sample is determined by the status of flow valves in cooperation with interconnected carrier gas and vacuum sources.

Such a cold trap as described above enables the trapping of both higher and lower boiling point compounds during substantially the same time period. Previously, such trapping was not possible because the lower boiling point compounds traversed the capillary tube before the higher boiling point compounds could be trapped. Conversely, if a PLOT column only was used in the cold trap, the lower boiling point compounds could be trapped, but the higher boiling point compounds are slow to elute during injection, backflushing and potentially contaminated the PLOT column.

In a second embodiment, the above described system interconnects to an analytical column to which is applied a source of carrier gas in proximity to its midpoint. The analytical column includes a precolumn portion between the cold trap and the carrier gas inlet and a postcolumn portion between the carrier gas inlet and a flame ionization detector. The two analytical portions enable backflushing the precolumn during application the carrier gas to the analytical column while simultaneously having the applied carrier gas sustain the flow of analyte in the postcolumn, thereby continuing analysis of higher boiling point compounds. The configuration of the second embodiment offers the above described advantages of the first embodiment and further decreases cycle time because backflushing and analysis can occur simultaneously.

Both the embodiments of this invention provide the additional benefit that the inlet system is continually flushed with carrier gas when collection is not taking place, thus further reducing the likelihood of the memory affect discussed previously.

Additional benefits and advantages of the present invention will become apparent to those skilled in the art to which this invention relates from the subsequent description of the preferred embodiments and the appended claims, taken in conjunction with the accompanying drawings.

BRIEF DESCRIPTION OF THE DRAWINGS

FIG. 7 is a schematic diagram similar to FIG. 4 except showing the fluid flow directions when the system is in an analysis and backflush mode.

DETAILED DESCRIPTION OF THE EMBODIMENT

Figure 1:
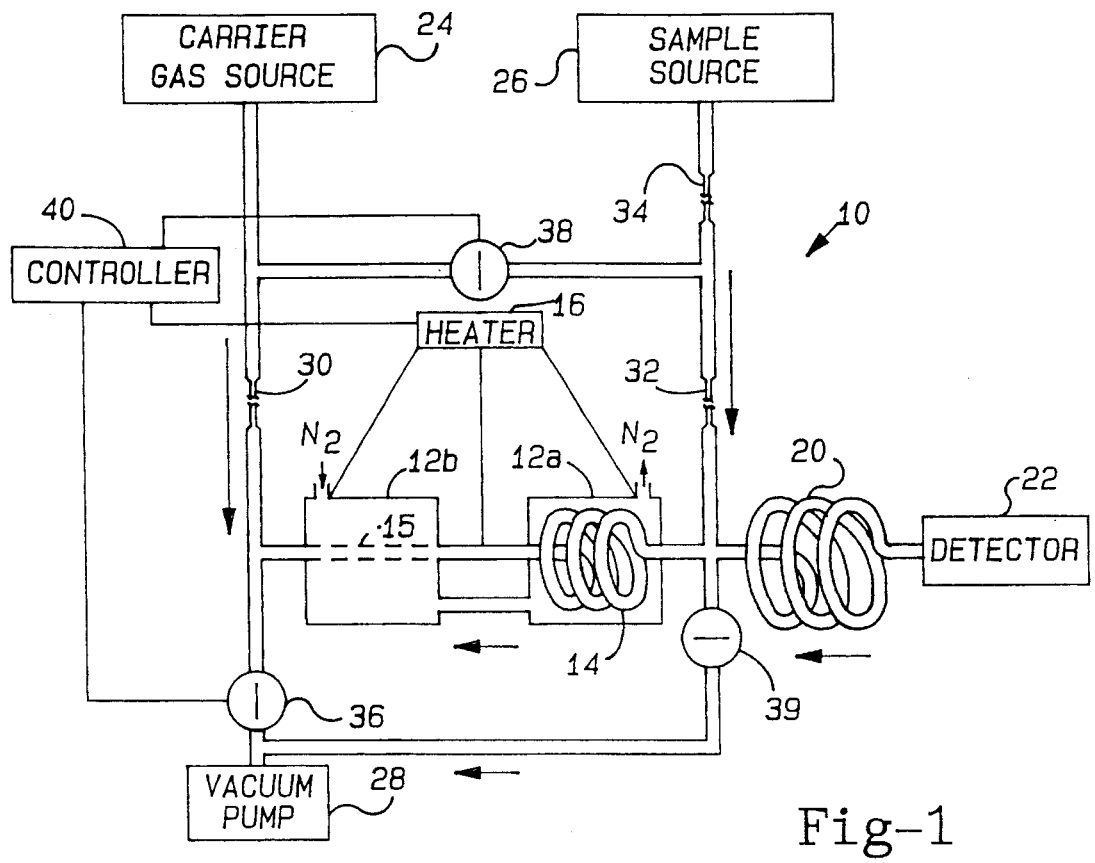
FIG. 1 is a schematic diagram of a gas chromatography system according to a first embodiment of this invention showing the direction of fluid flow when the system is in the collection mode.
Figure 2:
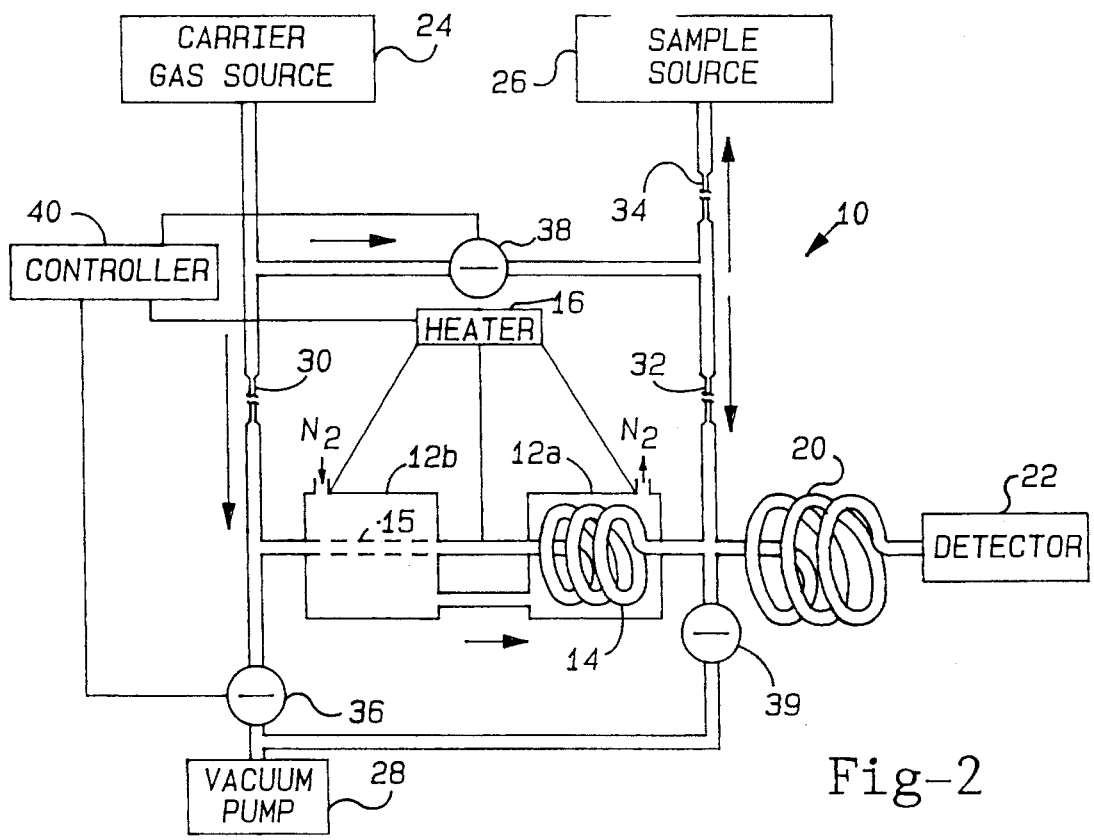
FIG. 2 is a schematic diagram similar to FIG. 1 showing the fluid flow directions when the system is in the injection mode.
Figure 3:
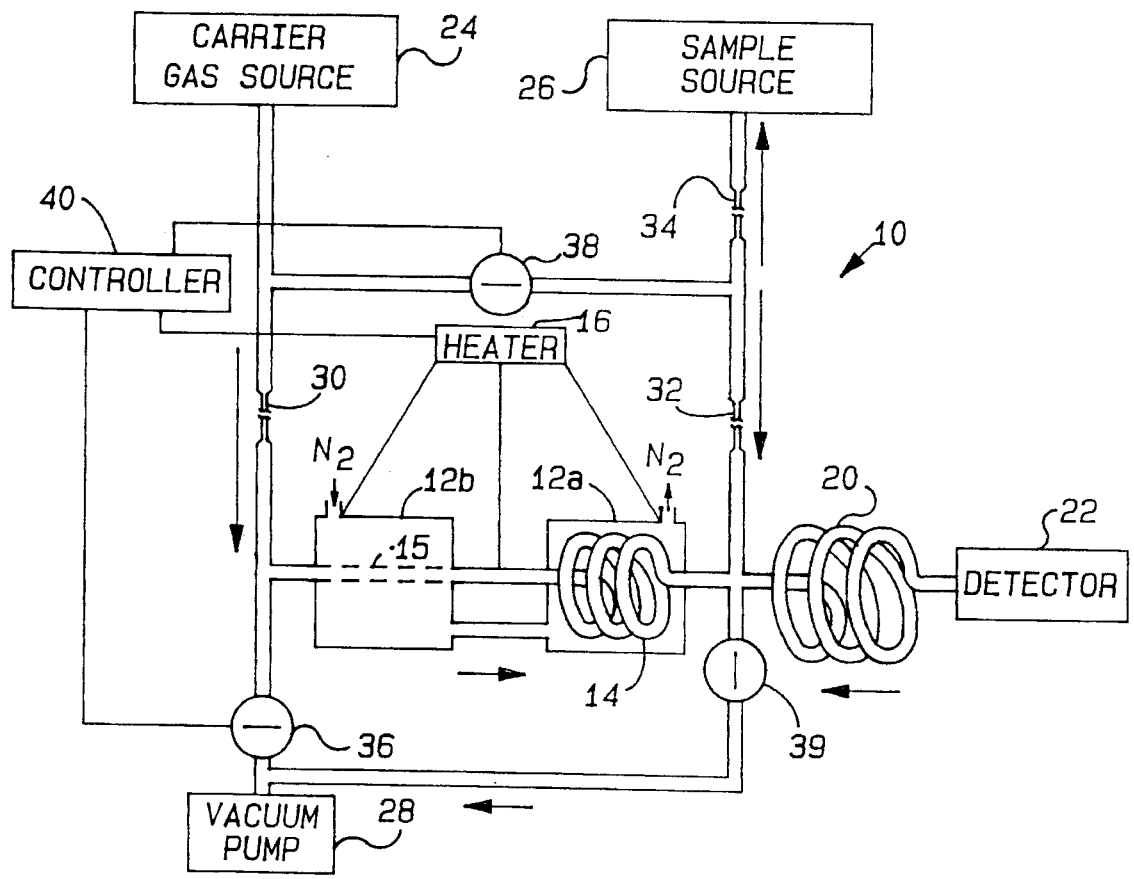
FIG. 3 is a schematic diagram similar to FIG. 1 except showing the fluid flow directions in a backflush mode.
Figure 4:
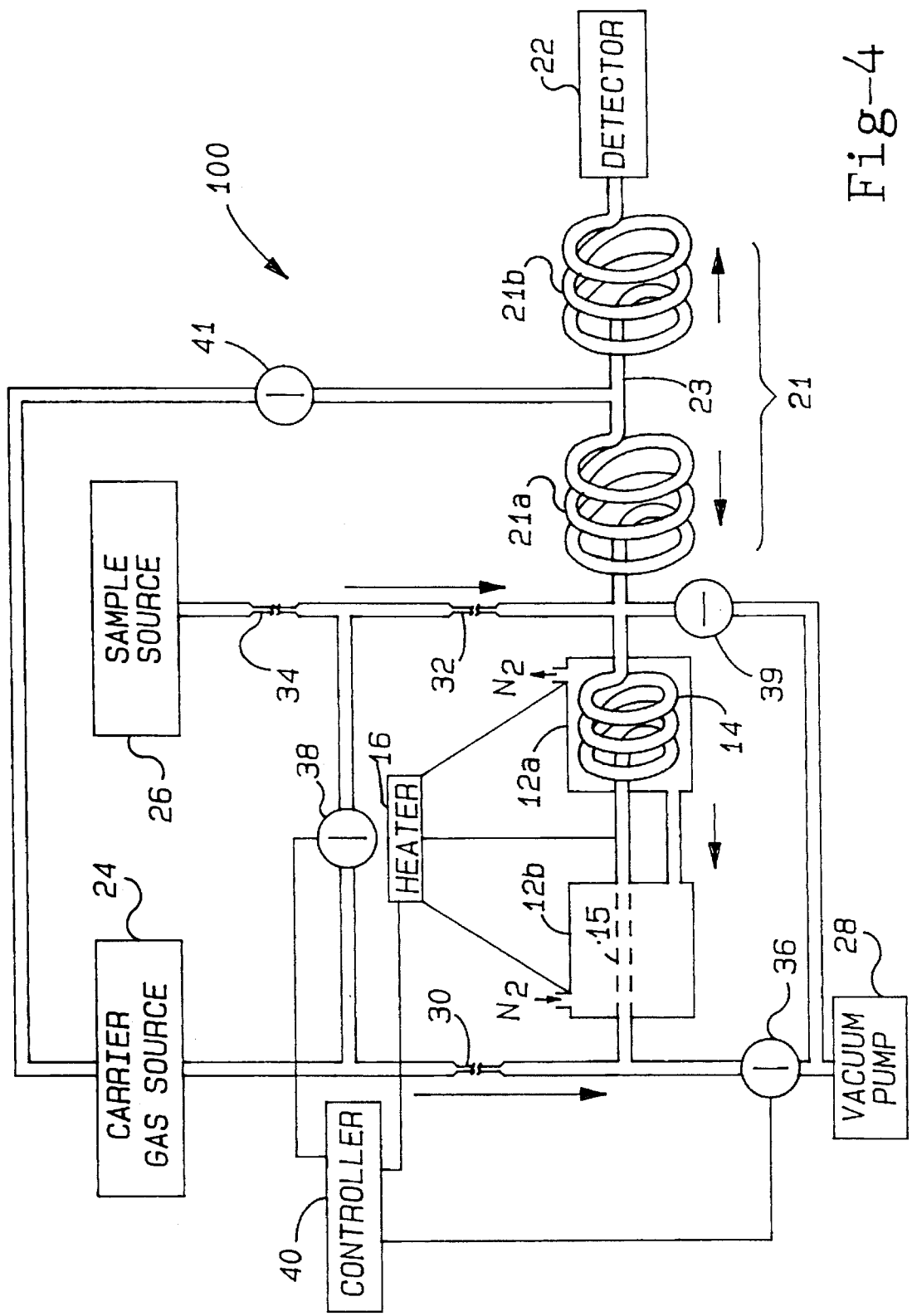
FIG. 4 is a schematic diagram of a gas chromatography system having a midpoint backflush separation column in accordance with a second embodiment of this invention when the system is in a sampling mode.

FIGS. 1, 2, and 3 provide a schematic diagram of a gas chromatography system in accordance with a first embodiment of this invention which is generally designated by reference number 10. As shown, gas chromatography system 10 includes a thermal focusing chamber or cold trap 12a–b having inlets and outlets for conducting the flow of a cryogenic gas such as nitrogen. Cold trap 12a–b is made up of two sections. A first section 12a may be referred to as a capillary tube section and houses a capillary tube 14 which effectuates trapping and focusing of higher boiling point compounds. A second portion of the cold trap 12a–b may be referred to as a porous layer open tubular (PLOT) trap 12b, comprising a PLOT column 15 which effectuates trapping and focusing of lower boiling point compounds that are not sufficiently trapped by and have traversed through capillary trap 12a. A metal capillary sample tube, referred to as capillary tube 14, passes through chamber 12a and conducts the analyte through the chamber. A length of a PLOT sample tube, referred to as PLOT column 15, passes through chamber 12b and conducts the analyte through chamber 12b.

A heater circuit 16 is separately connected to metal sample tube 14 and PLOT column 15 via a pair of conductive block or soldered connections for each of the capillary tube chamber 12b and the PLOT column chamber 12b, and a common connection between the chambers provides the potential for individual heating control for each chamber 12a and 12b. Heater 16 provides a short duration, high current pulse which causes extremely rapid heating of the sample tube. One such heater circuit which can be employed in conjunction with this invention is a multi-stage capacitive discharge circuit such as described in U.S. Pat. No. 5,096,471, herein incorporated by reference.

Sample tube 14 is also connected to gas chromatography separation column 20 which is preferably a fused silica capillary tube. The opposite end of column 20 is connected to detector 22 which may be a flame ionization detector (FID). Carrier gas source 24 provides the source of a carrier gas such as hydrogen or helium and communicates with PLOT column 15 through a conduit branch. Sample source 26 provides a sample at a pressure which is less than that of carrier gas source 24 and may be at ambient pressure or below and connects at the intersection between sample tube 14 and column 20 through another conduit branch. Vacuum pump 28 communicates with one end of PLOT column 15 and provides a low pressure of about a few Torr. As shown, various pneumatic restrictors 30, 32, and 34 control the flow rates of fluids through the various flow paths and are comprised of varying lengths of capillary tube.

A trio of valves 36, 38, and 39 are provided which are preferably pneumatically or electrically controlled on/off valves. As shown, valve 38 controls the flow of fluids between the carrier gas and sample flow paths, valve 36 exposes one end of PLOT column 15 to vacuum pump 28, and valve 39 exposes one end of capillary tube 14 and separation column 20 to vacuum pump 28. In an alternate embodiment (not shown), valve 36 could be eliminated in favor of a vacuum pump 28 which inherently performs the function of valve 36 when not energized, and valve 39 could be eliminated in favor of a second vacuum pump which inherently performs the function of valve 39 when not energized. Operation of valves 36, 38, and 39, and heater 16 is coordinated by controller 40.

Now with reference to FIGS. 1, 2 and 3, the operation of system 10 will be described. The arrows in the figures indicate the direction of fluid flow in the various modes of operation. FIG. 1 represents system 10 in a collection mode of operation. In this mode, valve 36 is opened and valves 38 and 39 are closed. By having valve 36 open, vacuum pump 28 serves as the lowest pressure point for the three separate flow paths originating at carrier gas source 24, sample source 26 and detector 22. Thus, fluids flow through all the flow paths toward vacuum pump 28. During this mode of operation, thermal focusing chambers 12a and 12b are at a low temperature and, therefore, some compounds of the sample condense on sample tube 14 as the sample is introduced into chamber 12a at its end closest to column 20. Alternatively, some of the lower boiling point compounds (such as methane) traverse sample tube 14 without condensing and, therefore, pass into PLOT column 15 of focusing chamber 12b. In this manner, the lower boiling point compounds do not escape focusing, but are focused in PLOT column 15 of focusing chamber 12b. The higher boiling point compounds condense in sample tube 14 of chamber 12a, do not traverse sample tube 14, and therefore do not reach PLOT column 15. Thus, chamber 12a partially acts as a filter to prevent the higher boiling point compounds from reaching PLOT column 15 of focusing chamber 12b. Such filtering is advantageous in decreasing the backflush time that would be required if merely a PLOT column such as PLOT column 15 were used to trap compounds of the sample, as the higher boiling point compounds would traverse PLOT column 15 significantly slower. Furthermore, some higher boiling point compounds could have a contaminating effect on PLOT column 15 if they were to reach PLOT column 15. Note also that a small amount of carrier gas is being continually vented at vacuum pump 28.

After a sample collection interval of, for example, several seconds, valve 38 is opened, valve 36 is closed, and valve 39 remains closed, which corresponds to the injection mode of operation. Simultaneously, a heating pulse is provided by heater circuit 16 to vaporize the collected sample. In this mode, detector 22 which is exposed to atmosphere constitutes a low pressure point of the system relative to the carrier gas source 24. The main flow of carrier gas in this mode is through restrictor 30 and then through PLOT trap 15, sample tube 14, and into column 20. A secondary forward flow of carrier gas originates from source 24 and travels through valve 38, restrictor 32 and then to column 20. The relative flow rates through these two paths are determined by the characteristics of restrictors 30 and 32. It is also significant that during this mode of operation a reverse flow occurs through restrictor 34 which has the effect of purging the conduit and restrictor 34, thus eliminating the remnants of prior samples from influencing subsequent evaluations. It should further be noted that the flow of carrier gas through restrictor 32 dilutes the sample being introduced to column 20 from thermal focusing chamber 12a–b. Accordingly, it is important to limit the flow rate through this pathway. As mentioned previously, during the injection mode, the samples which have collected at the outlet sides of each of PLOT trap 15 and sample tube 14 exit their respective trapping tubes without passing through the remainder of their respective sample tubes.

Several key elements of this invention will be noted at this time. First, the heating pulse discussed above provided by heater circuit 16 to vaporize the collected sample may be applied in any number of varied manners. For example, heater circuit 16 may provide a heating pulse simultaneously to both focusing chambers 12a and 12b to effectuate an increase in temperature of the sample tube 15 and PLOT column 15, respectively, substantially simultaneously. Second, the magnitude of the heating pulse for each of focusing chambers 12a and 12b may be varied between the focusing chambers to effectuate a varying degree of heating in one focusing chamber as compared to the other focusing chamber. This varied degree of heating may be directed to the specific requirements of each particular focusing chamber. Third, the duration of each heating pulse applied to each focusing chamber 12a and 12b may be varied in accordance with the specific heating needs of the sample to be trapped and the sample tube 14 and PLOT column 15, respectively. Fourth, while in some applications it may be desirable to perform detection only on the lower boiling point compounds trapped by focusing chamber 12b, a beneficial affect of trapping higher boiling point compounds at the sample tube 14 end closest to detection column 20 is realized through minimizing the travel distance of the higher boiling point compounds which may traverse sample tube 14 much more slowly than the higher boiling point compounds after application of the heating pulse and increased pressure of the carrier gas. Because the lower boiling point compounds trapped in focusing chamber 12b are likely to traverse sample tube 14 quickly and pass the higher boiling point compounds during injection into separation column 20, the lower boiling point compounds will pass through the separation column 20 much more quickly, leaving the higher boiling point compounds closer to the inlet end of separation column 20 in anticipation of backflushing the column, to be described herein with respect to FIG. 3.

FIG. 3 illustrates gas chromatography system 10 during a backflush mode of operation in which both valves 38 and 39 are open and valve 36 is closed. In this mode, both carrier gas source 24 and detector 22 serve as high pressure points for the system whereas vacuum pump 28 defines the low pressure point. Any analyte components remaining in column 20 will be directed in a reverse direction than injection, through valve 39 where they can be vented through vacuum pump 28. If the trap is maintained at a high temperature, the components that have not exited either of focusing chambers 12a or 12b exit cold trap 12a–b and are directed through valve 39 where they also may be vented through vacuum pump 28.

Alternatively, valve 39 may remain closed while valve 36 is opened in order to redirect any analyte components remaining in column 20 back into thermal focusing chambers 12a–b where they may be refocused if the trap is maintained at a cold temperature or, but not preferably, vented through vacuum pump 28. Venting of the analyte components through cold trap 12a–b and vacuum pump 28 is not preferred because the higher boiling point components typically traverse PLOT column 15 more slowly than when venting through valve 39 and vacuum pump 28. Nevertheless, this system can be used to provide a retrapping and reinjection mode as described in the parent of this application. Since valve 38 is open there remains a purge flow from carrier gas source 24 to the sample source 26 (which is at a lower pressure than the carrier gas source). Therefore, the system is not subject to contamination from the sample inlet during backflushing.

In order to provide the desired fluid flow directions and relative flow rates, it will be necessary to select the value of restrictors 30, 32, and 34 in accordance with the specific requirements of a particular application. In some instances, separate restrictor elements may be unnecessary due to the inherent flow restriction characteristics of various conduits used to form the system.

In an experimental prototype of the first embodiment, column 20 comprises a 4.0 meter long, 0.25 mm. i.d. fused silica capillary tube containing a 0.25 microns thick methyl silicone stationary phase. Each of the restrictors were formed from 0.1 mm. fused silica deactivated capillary tubes with restrictors 30, 32 and 34 having lengths of 25 cm., 60 cm. and 25 cm., respectively. Valves 36, 38, and 39 are low dead volume, electrically actuated solenoid valves. The vacuum pump 28 used was a Central Scientific HYVAC 7, two-stage pump. Sample tube 14 comprises a 0.30 mm I.D. Cu/Ni capillary tube, and PLOT column 15 comprises a 0.32 mm I.D. PoraPLOT Q tube.

As briefly described previously, gas chromatography system 10 possesses a number of significant advantages. A series cold trap 12a–b as described herein enables the trapping of lower boiling point compounds in PLOT column 15 while filtering the higher boiling point compounds in capillary tube 14, thereby preventing the higher boiling point compounds from entering PLOT column 15. This enables a much more efficient trapping mechanism for lower boiling point compounds, such as methane, which is virtually untrapable in capillary tube 14. A second advantage is realized during the injection cycle because the higher boiling point compounds trapped in capillary tube 14 will exit capillary tube 14 much more quickly than had they been trapped in PLOT trap 15. Third, some higher boiling point compounds could possibly contaminate the PLOT trap 15, thereby reducing the accuracy of subsequent analysis using cryofocusing.

In addition, a number of advantages inherent to a reverse sampling system are realized. These advantages include reduced decomposition of sample attributed to vaporization in a thermal focusing chamber, reduced maximum temperature to which the sample is exposed, reduced system dead volume, extended service life of sample tube 14. Furthermore, none of valves 36, 38, or 39 are in the flow path of the sample components, thus substantially minimizing the memory effect and sample contamination. Also, inlet system is continually purged when sample collection is not taking place which further minimizes the memory effect. And finally, since system 10 pulls a sample from source 26 using vacuum pump 28, the system is applicable to a wide range of inlet environments including direct air monitoring.

FIGS. 4–7 provide a schematic diagram of a second embodiment of a gas chromatography system in accordance with this invention which is generally designated by reference number 100. In FIGS. 4–7, many of the components described perform substantially similar functions as those components described in FIGS. 1–3. In such instances, like components will utilize identical reference numerals from FIGS. 1–3.

Gas chromatography system 100 includes a thermal focusing chamber or cold trap 12a–b, as described with respect to FIGS. 1–3, having inlets and outlets for conducting the flow of a cryogentic gas such as nitrogen. Gas chromatography system 100 also has a heater circuit 16 connected as described in FIGS. 1–3. One end of sample tube 14 is connected to gas chromatography analytical column 21 having a precolumn 21a portion and an postcolumn 21b portion meeting at column midpoint 23 and is preferably a fused silica capillary tube. Note that the respective portions of analytical separation columns 21 are both separation columns and are referred to as pre and post analytical columns to define their positions relative to their interconnection at midpoint 23. The end of postcolumn 21b opposite the connection with precolumn 21a is connected to FID 22. Carrier gas source 24 provides the source of a carrier gas such as hydrogen or helium and communicates with one end of PLOT trap 15. Carrier gas source 24 also communicates with precolumn 21a at midpoint 23 through an additional conduit branch. Sample source 26 provides a sample at a pressure which is less than that of carrier gas source 24 and may be at ambient pressure or below and is connected to sample tube 14 and precolumn 21a through another conduit branch. Vacuum pump 28 communicates with one end of PLOT trap 15 and provides a vacuum pump pressure lower than the sample pressure on the order of about a few Torr. Various pneumatic restrictors 30, 32, and 34 are provided which are comprised of varying lengths of capillary tube which are used to control the flow rates of fluids through the various flow paths.

A number of valves 36, 38, 39, and 41 are provided which are preferably pneumatically or electrically controlled on/off valves as described with respect to FIGS 1–3. As shown, valve 38 controls the flow of fluids between the carrier gas and sample flow paths, valve 36 exposes the inlet end of PLOT column 15 to vacuum pump 28, valve 39 controls fluid flow between the inlet end of precolumn 21a and vacuum source 28, and valve 41 controls fluid flow between carrier gas source 24 and column midpoint 23. As described with respect to FIGS. 1–3, valves 36 and 39 could be eliminated in favor of a vacuum pump which inherently performs the function of the respective valves. Operation of valves 36, 38, 39, and 41, and heater 16 is coordinated by controller 40.

Figure 5:
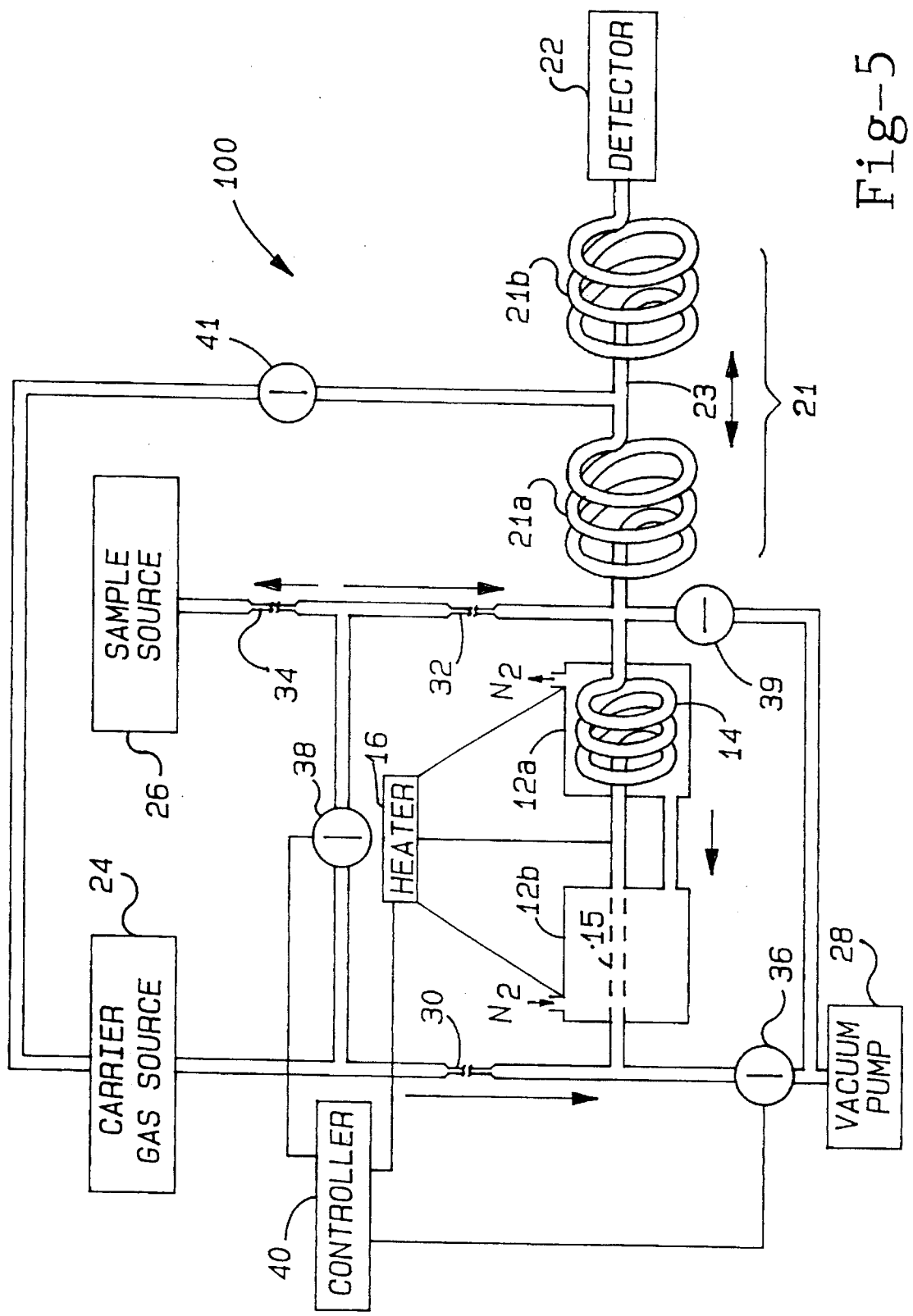
FIG. 5 is a schematic diagram similar to FIG. 4 except showing the fluid flow directions when the system is in an inlet flush mode.

Now with reference to FIGS 4–7, the operation of system 100 will be described. FIG. 1 represents system 100 in a collection mode of operation. In this mode, valves 36 and 41 are opened and valves 38 and 39 are closed. By having valve 36 open, vacuum pump 28 serves as the lowest pressure point for the three separate flow paths originating at carrier gas source 24, sample source 26, and midpoint 23. Thus, fluids flow through all the flow paths toward vacuum pump 28. During this mode of operation, as described with respect to FIGS 1–3, cold trap 12a–b is at a low temperature and, therefore, the sample condenses on sample tube 14 and some of the sample condenses on PLOT column 15 as it is being introduced into chamber 12a–b at its end closest to precolumn 21a. A small amount of carrier gas is being continually vented at vacuum pump 28. For a brief interval (0.5–1.0 seconds), valve 38 is then opened in order to purge sample source 26 and to enable the remainder of the sample to be pulled into cold trap 12a–b. The direction of fluid flow is indicated in FIG. 5 for this inlet flush operation. This operation is significant in that it has the effect of purging the conduit and the restrictor 34, thus eliminating the remanent of prior samples from influencing subsequent evaluation.

Figure 6:
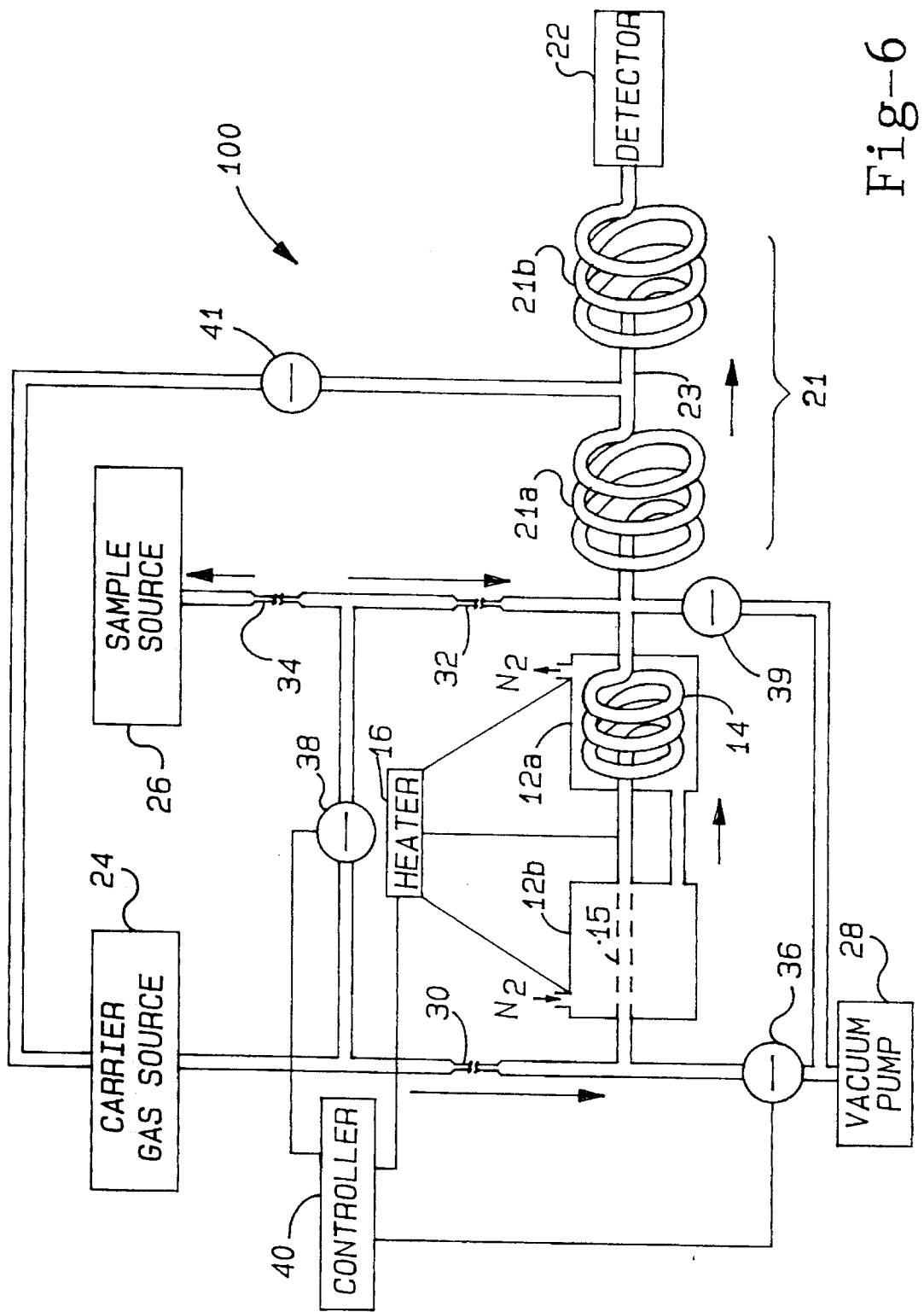
FIG. 6 is a schematic diagram similar to FIG. 4 except showing the fluid flow directions when the system is in an analysis mode.

After a sample collection interval of, for example, several seconds, valve 38 remains opened and valve 36 is closed to effectuate an injection mode of operation as shown in FIG. 6. Simultaneously, a heating pulse is provided by a heater circuit 16 to vaporize the collected sample. The variations on the application of a heating pulse are as described with respect to FIGS 1–3. In this mode, detector 22 which is exposed to atmosphere constitutes a low pressure point of the system relative to the carrier gas source 24. The main flow of carrier gas in this mode is through restrictor 30, through PLOT column 15, through sample tube 14, through precolumn 21a and postcolumn 21b, and into FID 22. A secondary forward flow of carrier gas originates from source 28 and travels through valve 38, restrictor 32, and then to precolumn 21a. The relative flow rates through these two paths are determined by the characteristics of restrictors 30 and 32. The flow of carrier gas through restrictor 32 dilutes the sample being introduced from cold trap 12a–b. Accordingly, it is important to limit the flow rate through this pathway.

FIG. 7 illustrates gas chromatography system 100 during a simultaneous analysis and backflush mode of operation in which valves 38, 39, and 41 are opened and valve 36 is closed. In this mode, carrier gas source 24 serves as a high pressure point for the system whereas vacuum pump 28 defines the low pressure point. Any analyte components remaining in precolumn 21a will reverse direction for venting through vacuum pump 28. Because valve 38 is open, there remains a purge flow from carrier gas source 24 to the sample source 26 (which is at a lower pressure than the carrier gas source). Therefore, the system is not subject to contamination from the sample inlet during backflushing.

Simultaneously with precolumn 21a being backflushed to remove the higher boiling point compounds which move through analytical column 21a–b at a much lower rate than the lower boiling point materials, the lower boiling point compounds flow from postcolumn 21b into FID 22 for analysis. Therefore, the lower boiling point materials that have passed the midpoint 23 precolumn 21a and postcolumn 21b continue to flow into detector 22 while the higher boiling point materials are backflushed. This split column design enables a decreased analysis time as the higher boiling point materials are backflushed through a shorter length of column, than a non-split column, simultaneously with the lower boiling point materials continuing to move through postcolumn 21b.

As with the apparatus in FIGS 1–3, in order to provide the desired fluid flow directions and relative flow rates, it will be necessary to select the value of restrictors 30, 32, and 34 in accordance with the specific requirements of a particular application. In some instances, separate restrictor elements may be unnecessary due to the inherent flow restriction characteristics of various conduits used to form the system.

In order for an analysis to continue without variation and retention times during column backflush, the pressure at the midpoint 23 must not change when valve 41 is opened because the fluid flow through valve 41 becomes the sole source of carrier gas to detector 22. If the pressure is set correctly, no change in the fluid flow rate to detector 22 should occur when valve 41 is opened. Final tuning of the backflush pressure may be established using sample injections and comparing the retention times of known components in the mixture with and without backflush. Shifts in elution time may be corrected by making adjustments to the pressure regulator (not shown) supplying carrier gas from carrier gas source 24. By properly regulating the pressure in the conduit branch providing supply gas to midpoint 25 of precolumn 21a and postcolumn 21b, it is possible to eliminate valve 41, but still obtain the same results in the absence of valve 41. Furthermore, the time at which backflushing is commenced is dependent upon the particular components desired to be removed during the analysis. The expected backflush initiation time may vary due to the pressure drop along the length of the column resulting from gas compressibility and having a precolumn 21a and postcolumn 21b midpoint 25 located such that the precolumn 21a and postcolumn 21a are slightly different lengths. Thus, the exact time needed for backflush start must be determined experimentally for the particular system being used.

As an example of a chromatography system as described in FIGS 4–7 herein, column 21 comprises a 26.0 meter long, 0.25 mm, i.d. fused silica capillary tube within a 0.25 microns thick methyl silicone stationary phase. The capillary tube 14 is a 0.30 mm ID Cu/Ni tube, and PLOT column 15 is a 0.32 mm ID PoraPLOT Q tube. Each of the restrictors are formed from 0.1 mm. i.d. fused silica deactivated capillary tubes with restrictors 30, 32, and 34 having lengths of 40 cm., 80 cm. and 40 cm., respectively. Valves 36, 38, 39, and 41 are 2 way, low dead volume valves and are electrically actuated. The carrier gas is applied continuously to yield a system pressure of 32.5 PSI and a midpoint 25 pressure of 20.0 PSI. The vacuum pump 28 used was 2-stage pump, but need not be limited to a 2-stage pump.

In addition to the advantages stated above with respect to FIGS 1–3, the following additional advantages are realized from the configuration presented in FIGS 4–7. Analysis time may be significantly decreased by backflushing precolumn 21a, while at the same time and using the same backflush pressure applied to precolumn 21a, continuing to analyze the sample in postcolumn 21b. Analysis time is further decreased as it is not necessary to wait for the high boiling point materials to elute from the analytical column because they are backflushed from the precolumn over a shorter distance while analysis of higher boiling point materials occurs substantially simultaneously.

While the above description constitutes the preferred embodiments of the present invention, it will be appreciated that the invention is susceptible of modification, variation and change without departing from the proper scope and fair meaning of the accompanying claims.

We claim:

1. A gas chromatography system comprising:

a source of a sample;

a source of a carrier gas;

a chromatography separation column;

a first sample tube having a first end and a second end, said first end communicating with said column and said source of a sample gas;

a second sample tube of a porous layer open tubular configuration having a first end communicating with the second end of said first sample tube and a second end communicating with said source of a carrier gas;

temperature adjustment means for controlling the temperature of said first sample tube between a first low temperature for condensing some components of said sample which thereby do not enter said second sample tube, and a first high temperature for vaporizing said some components, and for controlling the temperature of said second sample tube between a second low temperature for condensing other components of said sample, and a second high temperature for vaporizing said other components;

a controllable pressure means for causing said sample to flow into said first sample tube second end;

control means for controlling said temperature adjustment means and said pressure means wherein during a collection mode, said pressure means draws said sample into said first sample tube first end through said first and second sample tubes while said first and second sample tubes are simultaneously at said first and second low temperatures, respectively, and during an injection mode, causes said sample tubes to be simultaneously heated to said first and second high temperatures, respectively, thereby vaporizing said some components and said other components and allowing said carrier gas to flow into said second sample tube second end, through said second sample tube and into said first sample tube second end, through said first sample tube, and into said column.

2. A gas chromatography system according to claim 1 wherein said controllable pressure means comprises a vacuum source communicating with said second sample tube second end.

3. A gas chromatography system according to claim 2 further comprising a first conduit branch communicating said source of carrier gas with said second sample tube second end, and a second conduit branch communicating said source of a sample with said first sample tube first end, with first valve means between said first and second branches for allowing fluid flow between said branches, wherein during said collection mode, said first valve means is closed causing said carrier gas to flow through said first branch into said vacuum source, and said sample to flow through said second branch and through said first sample tube toward said vacuum source.

4. A gas chromatography system according to claim 3 wherein during said injection mode, said first valve means is opened allowing said carrier gas to flow through at least a portion of said second branch thereby flushing said portion.

5. A gas chromatography system according to claim 3 wherein said control means further controls said gas chromatography system to provide a backflush mode in which said source of vacuum is actuated and said first valve means is opened allowing said column and said second conduit branch to be purged.

6. A gas chromatography system according to claim 3 further comprising a first fluid restrictor means in said second branch between said first valve means and said sample source and a second fluid restrictor means in said second branch between said first valve means and said column, wherein said restrictors control the flow of fluids during said modes of operation.

7. A gas chromatography system according to claim 3 further comprising a third fluid restrictor means in said first conduit branch between said first valve means and said second sample tube for controlling the flow of fluids during said modes of operation.

8. A gas chromatography system according to claim 3 wherein said vacuum source comprises a vacuum pump and a second valve means.

9. A gas chromatography system according to claim 3 further comprising a third conduit branch communicating the inlet end of said column with said vacuum source and a third valve means, said third valve means being open and said first valve means being closed to provide a backflush mode of operation.

10. A gas chromatography system according to claim 3 wherein said separation column includes two separation columns communicating at a midpoint and a fourth conduit branch communicating said source of carrier gas with said midpoint.

11. A gas chromatography system comprising:

a source of a sample;

a source of a carrier gas;

a chromatography separation column;

a first sample tube in the form of a metal capillary tube;

a second sample tube having a porous layer open tubular configuration;

temperature adjustment means for controlling the temperature of said first sample tube between a first low temperature for condensing some components of said sample, and a first high temperature for vaporizing said some components and for controlling the temperature of said second sample tube between a second low temperature for condensing other components of said sample, and a second high temperature for vaporizing said other components; and fluid circuit and control means for causing said sample to flow into said first and second sample tubes in a first flow direction during a collection mode during which said first and second sample tubes are simultaneously at said first and second low temperatures and whereby said some components condensing on said first sample tube are prevented from entering said second sample tube, respectively, and causing said carrier gas to flow through said first and second sample tubes in an opposite second direction during an injection mode, during which said first and second sample tubes are simultaneously at said first and second high temperatures, respectively.

12. A gas chromatography system according to claim 11 wherein said fluid circuit and control means further comprises said second sample tube having a first and second end, said second end communicating with said source of a carrier gas and having a first end communicating with a second of said first sample tube, and said first sample tube also has a first end communicating with said column.

13. A gas chromatography system according to claim 12 further comprising a controllable pressure means for causing said sample to flow into said first tube first end in said first direction during said collection mode.

14. A gas chromatography system according to claim 13 wherein said controllable pressure means comprises a vacuum source communicating with said second sample tube second end.

15. A gas chromatography system according to claim 14 further comprising a first conduit branch communicating said source of carrier gas with said second sample tube second end, and a second conduit branch communicating said source of a sample to said first sample tube first end, with first valve means between said first and second branches for allowing fluid flow between said branches, wherein during said collection mode, said first valve means is closed causing said carrier gas to flow through said first branch and toward said vacuum source, and said sample to flow through said branch and through said first and second sample tubes in said first direction toward said vacuum source.

16. A gas chromatography system according to claim 15 wherein during said injection mode, said first valve means is opened allowing said carrier gas to flow through at least a portion of said second branch thereby flushing said portion.

17. A gas chromatography system according to claim 14 wherein said control means further controls said gas chromatography system to provide a backflush mode in which said source of vacuum is actuated and said first valve means is opened allowing said vacuum and said second conduit branch to be purged.

18. A gas chromatography system according to claim 15 further comprising a first fluid restrictor means in said second branch between said first valve means and said sample source and a second fluid restrictor means in said second branch between said first valve means and said column, wherein said restrictors control the flow of fluids during said modes of operation.

19. A gas chromatography system according to claim 15 further comprising a third restrictor means in said first conduit branch between said first valve means and said sample tube, for controlling the flow of fluids during said modes of operation.

20. A gas chromatography system according to claim 14 wherein said vacuum source comprises a vacuum pump and a second valve means.

21. A gas chromatography system according to claim 15 further comprising a third conduit branch communicating the inlet end of said column with said vacuum source and a third valve means, said third valve means being open and said first valve means being closed to provide a backflush mode of operation.

22. A gas chromatography system according to claim 15 wherein said separation column includes two separation columns communicating at a midpoint and a fourth conduit branch communicating said source of carrier gas with said midpoint.

23. A gas chromatography system comprising:
  a source of a sample;
  a source of a carrier gas;
  a chromatography separation column;
  a first sample tube of a bare metal capillary tube configuration in fluid communication with said column having an inlet end and an outlet end;
  a second sample tube of a porous layer open tubular configuration in fluid communication with said source of a carrier gas having an inlet and an outlet;
  a temperature adjustment means for controlling the temperature of said first sample tube between a first low temperature for condensing some components of said sample, and a first high temperature for vaporizing said some components and for controlling the temperature of said second sample tube between a second low temperature for condensing other components of said sample, and a second high temperature for vaporizing said other components;
  a controllable source of vacuum communicating between said first and said second sample tubes and said column;
  first restrictor means communicating with said carrier gas source and said second sample tube second end;
  second restrictor means communicating said sample source and said first sample tube first end; and
  control means for providing a collection mode energizing said vacuum source for drawing said carrier gas and said sample source through said restrictors into said first and second sample tubes while said first and second sample tubes are simultaneously at said first and second low temperatures, respectively, and in an injection mode deactivating said vacuum source causing said carrier gas to purge said second restrictor and injecting said sample into said column as said first and second sample tubes are simultaneously at said first and second high temperatures, respectively.

24. A gas chromatography system according to claim 23 wherein said sample source comprises ambient air.

25. A gas chromatography system comprising;
  a source of sample;
  a source of carrier gas;
  a split chromatography separation column, the split separation column having a precolumn communicating with a postcolumn;
  a first sample tube in the form of a metal capillary tube having a first end and a second end, said first end communicating with said column and said source of a sample gas;
  a second sample tube of a porous layer open tubular configuration having a first end communicating with the second end of said first sample tube and a second end communicating with said source of a carrier gas;
  a backflush circuit having a first end communicating with the source of a carrier gas and a second end communicating with the precolumn and the postcolumn;
  temperature adjustment means for controlling the temperature of said first sample tube between a first low temperature for condensing some components of said sample, and a first high temperature for vaporizing said some components, and for controlling the temperature of said second sample tube between a second low temperature for condensing other components of said sample, and a second high temperature for vaporizing said other components;
  pressure control means for causing the sample to flow into the second end of the sample tube;
  control means for controlling said temperature adjustment means and said pressure means wherein during a collection mode, said pressure means draws said sample into said first sample tube first end through said first and second sample tubes while said first and second sample tubes are simultaneously at said first and second low temperatures, respectively, and during an injection mode, causes said sample tubes to be simultaneously heated to said first and second high temperatures, respectively, and allowing said carrier gas to flow into said second sample tube second end, through said second sample tube and into said first sample tube second end, through said first sample tube, and into said column precolumn to effectuate injection, and to enable the carrier gas to flow into the first end of the backflush tube, through the backflush tube, into the precolumn to effectuate backflushing of the precolumn and the sample tube while enabling continued analysis of the sample gas in the postcolumn.

26. A gas chromatography system as defined in claim 25 wherein said pressure control means further comprises a vacuum source communicating with said sample tube first end.

27. A gas chromatography system as defined in claim 26 further comprising a first conduit branch communicating the source of carrier gas with said second sample tube second end, and a second conduit branch communicating the source of a sample with said first sample tube first end, with first valve means between said first and second branches for allowing fluid flow between said branches, wherein during the collection mode, said first valve means is closed, causing said carrier gas to flow through said first branch into the vacuum source, and said sample to flow through said second conduit branch and through said first sample tube towards said vacuum source.

28. A gas chromatography system as defined in claim 27 wherein during said injection mode, said first valve means is opened, allowing said carrier gas to flow through at least a portion of the second conduit branch thereby flushing the portion of the second conduit branch.

29. A gas chromatography system as defined in claim 27 wherein said control means further controls said gas chromatography system to provide a backflush mode in which said vacuum source is actuated and said first valve means is opened, allowing said column, said second conduit branch, and the cold trap to be purged while sample gas in said postcolumn is responsive to pressure to advance in a forward direction in said analytical column.

30. A gas chromatography system as defined in claim 27 further comprising a first fluid restrictor means in said second conduit branch between said first valve means and said sample source and a second fluid restrictor means in said second branch between said first valve means and said column, wherein said restrictors control the flow of fluids during the modes of operation.

31. A gas chromatography system as defined in claim 27 further comprising a third fluid restrictor means in said first conduit branch between said first valve means and said second sample tube for controlling the flow of fluids during said modes of operation.

32. A gas chromatography system as defined in claim 27 wherein said vacuum source further comprises a vacuum pump and a second valve means.

33. A gas chromatography system as defined in claim 27 wherein said backflush tube further comprises a third valve means to enable carrier gas to flow into said precolumn and said postcolumn during backflush mode.

34. A gas chromatography system as defined in claim 27 wherein the vacuum source supplies a pressure lower than the source of sample.

35. A gas chromatography system according to claim 27 further comprising a third conduit branch communicating the inlet end of said column with said vacuum source and a third valve means, said third valve means being open and said first valve means being closed to provide a backflush mode of operation.

36. A gas chromatography system according to claim 27 wherein said separation column includes two separation columns communicating at a midpoint and a fourth conduit branch communicating said source of carrier gas with said midpoint.

* * * * *